(12) United States Patent
Ekberg et al.

(10) Patent No.: US 10,221,392 B2
(45) Date of Patent: Mar. 5, 2019

(54) GENERATION OF PANCREATIC ENDODERM FROM PLURIPOTENT STEM CELLS USING SMALL MOLECULES

(71) Applicants: Novo Nordisk A/S, Bagsvaerd (DK); Takara Bio Europe AB, Gothenburg (SE)

(72) Inventors: Jenny Ekberg, Malmoe (SE); Mattias Hansson, Malmoe (SE); Ulrik Doehn, Veskoe (DK); Katja Hess, Heidelberg (DE); Nina Funa, Lund (SE)

(73) Assignees: Novo Nordisk A/S, Bagsværd (DK); TAKARA BIO EUROPE AB, Gothenburg (SE)

( * ) Notice: Subject to any disclaimer, the term of this patent is extended or adjusted under 35 U.S.C. 154(b) by 0 days.

(21) Appl. No.: 15/215,807

(22) Filed: Jul. 21, 2016

(65) Prior Publication Data
US 2016/0326495 A1    Nov. 10, 2016

Related U.S. Application Data

(62) Division of application No. 14/425,136, filed as application No. PCT/EP2013/068188 on Sep. 3, 2013.

(60) Provisional application No. 61/697,970, filed on Sep. 7, 2012.

(30) Foreign Application Priority Data

Sep. 3, 2012  (EP) .................................... 12182747
Dec. 21, 2012  (EP) .................................... 12198820

(51) Int. Cl.
*C12N 5/071*    (2010.01)

(52) U.S. Cl.
CPC ......... *C12N 5/0676* (2013.01); *C12N 5/0678* (2013.01); *C12N 2501/115* (2013.01); *C12N 2501/117* (2013.01); *C12N 2501/119* (2013.01); *C12N 2501/155* (2013.01); *C12N 2501/16* (2013.01); *C12N 2501/385* (2013.01); *C12N 2501/41* (2013.01); *C12N 2501/415* (2013.01); *C12N 2501/60* (2013.01); *C12N 2501/727* (2013.01); *C12N 2501/999* (2013.01); *C12N 2503/02* (2013.01); *C12N 2506/02* (2013.01); *C12N 2506/45* (2013.01)

(58) Field of Classification Search
None
See application file for complete search history.

(56) References Cited

U.S. PATENT DOCUMENTS

2007/0259423 A1    11/2007  Odorico et al.
2009/0263896 A1    10/2009  Kelly et al.
2009/0325294 A1    12/2009  Nelson
2010/0028307 A1    2/2010   O'Neil
2010/0112691 A1    5/2010   Green et al.
2011/0151560 A1    6/2011   Xu

FOREIGN PATENT DOCUMENTS

| EP | 2505639 A1 | 12/2009 |
|---|---|---|
| EP | 2233566 A1 | 9/2010 |
| WO | 03029445 A1 | 4/2003 |
| WO | 03068357 A2 | 8/2003 |
| WO | 2005005608 A2 | 1/2005 |
| WO | 2005086860 A2 | 9/2005 |
| WO | 2006134017 A2 | 12/2006 |
| WO | 2007/103282 A2 | 9/2007 |
| WO | 2007127927 A2 | 11/2007 |
| WO | 2008036447 A2 | 3/2008 |
| WO | 2008048671 A1 | 4/2008 |
| WO | 09012428 A2 | 1/2009 |
| WO | 2009006399 A1 | 1/2009 |
| WO | 2009018453 A1 | 2/2009 |
| WO | 2009048675 A1 | 4/2009 |
| WO | 2009096902 A1 | 8/2009 |
| WO | 2009131568 A1 | 10/2009 |
| WO | 2009132063 A2 | 10/2009 |
| WO | 2009132083 A2 | 10/2009 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2010091241 A2 | 8/2010 |
| WO | 2010124142 A2 | 10/2010 |
| WO | 2010136583 A2 | 12/2010 |
| WO | 2011011302 A2 | 1/2011 |

(Continued)

OTHER PUBLICATIONS

Mfopou J K et al., Noggin, Retinoids, and Fibroblast Growth Factor Regulate Hepatic or Pancreatic Fate of Human Embryonic Stem Cells, Journal: Gastroenterology, vol. 138, Year: 2010, pp. 2233-2245.

Leon-Quinto T et al, In vitro directed differentiation of mouse embryonic stem cells into insulin-producing cells, Journal: Diabetologia, vol. 47, Year: 2004, pp. 1442-1451.

Shiraki N et al., Guided Differentiation of Embryonic Stem Cells into Pdx1-Expressing Regional-Specific Definitive Endoderm, Journal: Stem Cells, vol. 26, Year: 2008, pp. 874-885.

Zhang D et al, Highly efficient differentiation of human ES cells and iPS cells into mature pancreatic insulin-producing cells, Journal: Cell Research, vol. 19, Year: 2009, pp. 429-438.

(Continued)

*Primary Examiner* — James D Schultz
(74) *Attorney, Agent, or Firm* — Leon Y. Lum

(57) ABSTRACT

A method of producing pancreatic cells or pancreatic cell precursors expressing at least 5% PDX1/NKX6.1 double positive, comprising exposing definitive endoderm cells to an effective amount of one or more small molecules, to differentiate the human definitive endoderm cells into the pancreatic cells or pancreatic cell precursors. The present invention also relates to pancreatic endoderm cells produced by said methods and uses of said pancreatic endoderm cells.

12 Claims, 5 Drawing Sheets

(56) References Cited

FOREIGN PATENT DOCUMENTS

| WO | 2011011349 A2 | 1/2011 |
| --- | --- | --- |
| WO | 2011079017 A2 | 6/2011 |
| WO | 2011079018 A2 | 6/2011 |
| WO | 2011081222 | 7/2011 |
| WO | 2011100291 A1 | 8/2011 |
| WO | 2011143299 A2 | 11/2011 |
| WO | 2012025914 A1 | 3/2012 |
| WO | 2012030540 A2 | 3/2012 |
| WO | 2012175633 A1 | 12/2012 |

OTHER PUBLICATIONS

Chen S et al., A small molecule that directs differentiation of human ESCs into the pancreatic lineage, Journal: Nature Chemical Biology, vol. 5, No. 4, Year: 2009, pp. 258-265.

Surmacz B et al., Directing Differentiation of Human Embryonic Stem Cells Toward Anterior Neural Ectoderm Using Small Molecules, Journal: Stem Cells, vol. 30, No. 9, Year: 2012, pp. 1875-1884.

Charton J et al., Novel non-carboxylic acid retinoids: 1,2,4-Oxadiazol-5-one derivatives, Journal: Bioorganic & Medicinal Chemistry Letters, vol. 19, No. 2, Year 2009, pp. 489-492.

Nostro M C et al., Stage-specific signaling through TGF[beta] family members and WNT regulates patterning and pancreatic specification of human pluripotent stem cells, Journal: Development, vol. 138, No. 5, Year: 2011, pp. 861-871.

Cuny G D et al., Structure-activity relationship study of bone morphogenetic protein (BMP) signaling inhibitors, Journal: Bioorganic & Medicinal Chemistry Letters, vol. 18, No. 15, Year: 2008, pp. 4388-4392.

Kroon E et al., Pancreatic endoderm derived from human embryonic stem cells generates glucose-responsive insulin-secreting cells in vivo. Journal: Nature Biotechnology, vol. 26, No. 4, pp. 443-452.

D'Amour et al., Production of pancreatic hormone-expressing endocrine cells from human embryonic stem cells, Journal: Nature Biotechnology, vol. 24, No. 11, Year: 2006, pp. 1392-1401.

Cai J et al., Generation of Homogeneous PDX1þ Pancreatic Progenitors from Human ES Cell-derived Endoderm Cells, Journal: Journal of Molecular Cell Biology, Year: 2010, vol. 2, pp. 50-60.

Ameri J et al., FGF2 Specifies hESC-Derived Definitive Endoderm into Foregut/Midgut Cell Lineages in a concentration-Dependent Manner, Journal: Stem Cells, vol. 28, Year 2010, pp. 45-56.

Kunisada Y et al., Small molecules induce efficient differentiation into insulin-producing cells from human induced pluripotent stem cells, Journal: Stem Cell Research, vol. 8, Year: 2012, pp. 274-284.

Schulz T C et al., A Scalable System for Production of Functional Pancreatic Progenitors from Human Embryonic Stem Cells, Journal: PLoS One, vol. 7, No. 5, Year: 2012, pp. 1-17.

Kim et al. "Signaling and Transcriptional Control of Pancreatic Organogenesis." Current Opinion in Genetics and Development 2002 vol. 12 pp. 540-547.

Calbiochem Merck Millipore.

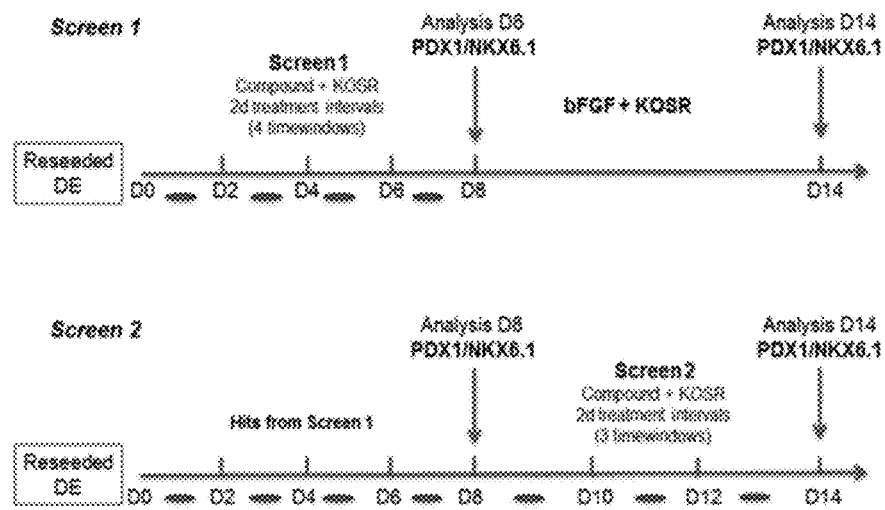
Fig. 4/6
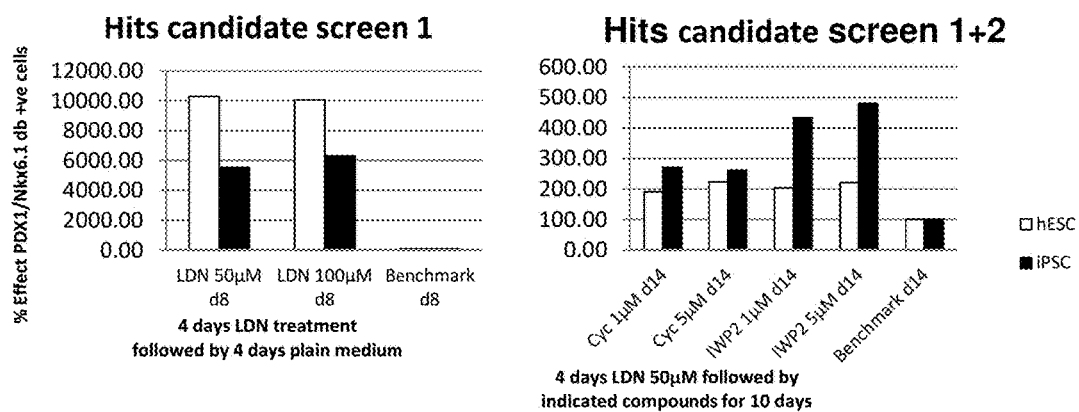
Fig. 5

GENERATION OF PANCREATIC ENDODERM FROM PLURIPOTENT STEM CELLS USING SMALL MOLECULES

CROSS-REFERENCE TO RELATED APPLICATIONS

This application is a divisional application of U.S. Ser. No. 14/425,136, filed Mar. 2, 2015 which is a 35 U.S.C. § 371 National Stage application of International Application PCT/EP2013/068188 (WO 2014/033322), filed Sep. 3, 2013, which claims priority to European Patent Application 12182747.1, filed Sep. 3, 2012 and European Patent Application 12198820.8, filed Dec. 21, 2012, the contents thereof which are incorporated by reference in their entirety; this application claims priority under 35 U.S.C. § 119 to U.S. Provisional Application 61/697,970, filed Sep. 7, 2012; the contents thereof which are incorporated by reference in their entirety.

TECHNICAL FIELD

The present invention relates to methods of generating pancreatic endoderm from pluripotent stem (PS) cells, such as human definitive endoderm.

BACKGROUND

Beta cell transplantation potentially provides the ultimate cure for type I diabetes. However, the limited availability of donor beta cells constrains the use of this treatment as a clinical therapy. Pluripotent stem cells can proliferate infinitely and differentiate into many cell types; thus, PS cells are a promising source for beta cells. However, before PS cells can be used to treat diabetes, they need to be efficiently and reproducibly differentiated to pancreatic cells.

During vertebrate embryonic development, a pluripotent cell gives rise to the three germ layers; ectoderm, mesoderm and endoderm. Induction of definitive endoderm (DE) is the first step towards formation of endoderm derived tissues. Generation of pancreatic endoderm (PE) from DE cells is necessary for the generation of insulin-producing beta cells. PE cells with the potential to become endocrine progenitors (EP) are characterized by co-expression of two important transcription factors, PDX1 and NKX6.1.

Stepwise in vitro differentiation protocols have been established for generating pancreatic cells from PS cells. These protocols generally mimic the major events of pancreatic development, which includes several stages such as formation of the DE which co-expresses SOX17 and FOXA2, primitive gut, posterior foregut, PE, EP and ultimately the mature beta cells. To date, efficient DE differentiation of hES cells has been achieved by activin A treatment. The next major step in generating pancreatic beta cells is to generate PE that co-expresses PDX1 and NKX6.1. Several groups have developed in vitro protocols that can differentiate PS cells into DE and PE, however they are only able to generate a modest fraction of NKX6.1/PDX1 double positive (db+ve) cells, and importantly none of them are able to generate fully mature beta cells in vitro (Cai et al. (2010); D'Amour et al. (2006); Kunisada et al. (2012); Schulz et al. (2012); Zhang et al. (2009); Ameri et al. (2010)).

SUMMARY

The present invention relates to a method of producing pancreatic cells or pancreatic cell precursors where at least 5% of the cells co-express PDX1 and NKX6.1, comprising exposing definitive endoderm (DE) cells to an effective amount of at least one compound of the group consisting of:
  a. BMP inhibitor LDN-193189 (listed in table 1)
  b. Kinase inhibitors (listed in tables 1 and 2)
  c. Retinoic acid receptor agonists (listed in table 2)
to differentiate the human DE cells into the pancreatic cells or pancreatic cell precursors.

The present invention further relates to a method for producing pancreatic cells or pancreatic cell precursors where at least 5% of the cells co-express PDX1 and NKX6.1, comprising exposing DE cells to an effective amount of at least one compound of the group consisting of:
  a. BMP inhibitor LDN-193189 (listed in table 1)
  b. isomers of 1,9-pyrazoloanthrone with or without N-alkylation (listed in table 1 and 2)
  c. Retinoic acid receptor agonists (listed in table 2)
to differentiate the human DE cells into the pancreatic or pancreatic cell precursors.

The present invention further relates to a method for producing pancreatic cells or pancreatic cell precursors where at least 5% of the cells co-express PDX1 and NKX6.1, comprising exposing definitive endoderm cells to an effective amount of at least one compound of the group consisting of:
  a. BMP inhibitor LDN-193189
  b. JNK inhibitor II
  c. AM580
to differentiate the human DE cells into the pancreatic or pancreatic cell precursors.

The present invention further relates to a method for generating pancreatic cells or pancreatic cell precursors where at least 5% of the cells co-express PDX1 and NKX6.1, comprising exposing definitive endoderm cells to an effective amount of the BMP inhibitor LDN-193189, to differentiate human DE cells into pancreatic or pancreatic cell precursors.

The present invention further relates to a method for generating pancreatic cells or pancreatic cell precursors where at least 5% of the cells co-express PDX1 and NKX6.1, comprising exposing DE cells to an effective amount of the BMP inhibitor LDN-193189, and subsequent exposure to one of the following molecules:
  a. Wnt inhibitor IWP2
  b. Hedgehog inhibitor Cyclopamine (Cyc)
to differentiate human DE cells into pancreatic or pancreatic cell precursors.

The present invention further relates to a method for generating pancreatic cells or pancreatic cell precursors where at least 5% of the cells co-express PDX1 and NKX6.1, comprising exposing DE cells to an effective amount of the BMP inhibitor LDN-193189, and subsequent exposure to a combination of JNK inhibitor II, retinoic acid or a retinoic acid derivative, bFGF and one of the following molecules:
  a. Wnt inhibitor IWP2
  b. Hedgehog inhibitor Cyclopamine
to differentiate human DE cells into pancreatic or pancreatic cell precursors.

The present invention further relates to a method for generating pancreatic cells or pancreatic cell precursors where at least 5% of the cells co-express PDX1 and NKX6.1, comprising exposing DE cells to an effective amount of the BMP inhibitor LDN-193189, and subsequent exposure to a combination of JNK inhibitor II in combination with retinoic acid or a retinoic acid derivative, bFGF and LDN-193189 to differentiate DE stem cells into pancreatic or pancreatic cell precursors.

In one embodiment of the present invention, any one of the retinoic acid receptor agonists or kinase inhibitors may be in combination with bFGF.

The present invention further relates to pancreatic cells or pancreatic cell precursors obtainable by the methods of the present invention.

The present invention relates to a pancreatic cell or pancreatic cell precursor produced by exposing a human pluripotent stem cell to at least one compound listed in tables 1 and 2.

The present invention relates to use of any one of the compounds of tables 1 and 2, to induce pancreatic cells or pancreatic cell precursors from stem cells.

The present invention relates to use of LDN-193189 to induce pancreatic cells or pancreatic cell precursors from stem cells.

The present invention relates to use of LDN-193189 followed by Cyclopamine or IWP2, to induce pancreatic cells or pancreatic cell precursors from stem cells.

The present invention takes an alternative approach to improve the efficiency of differentiating human PS cells toward mature beta cells, by providing a method to increase the fraction of NKX6.1/PDX1 double positive cells, a hallmark for PE cells committed to an endocrine cell fate.

In one aspect, the invention provides an improved pancreatic cell population, i.e. PE with increased fraction of NKX6.1/PDX1 double positive cells.

Furthermore, the present invention provides a more homogenous pancreatic cell population, which is important for the further development of these cells towards the endocrine lineage.

The present invention also provides a more synchronised pancreatic population to get to the next stage.

The present invention may also solve further problems that will be apparent from the disclosure of the exemplary embodiments.

BRIEF DESCRIPTION OF DRAWINGS

FIG. 4 shows a second, candidate based PE screening approach. Pluripotent stem (PS) cells were differentiated into definitive endoderm according to DE protocol (See general methods) and seeded in 96 well plates for screening. The pancreatic endoderm screen was divided into two parts. In screen 1, compounds were added to a basal medium (RPMI1640+0.1% PEST+12% KOSR) the first eight days of PE differentiation. Compounds were tested in 4 different time windows having 2 day increments and then cells were left to continue differentiation for another six days in the bFGF based published protocol (Ameri et al., 2010). In screen 2, cells were first differentiated for 4 days with the hit compounds from screen 1, then screening compounds were added the last 10 days to basal medium.

FIG. 5 shows hits from the candidate screen 1 and 2 compared to cells differentiated according to Ameri et al, 2010 which was used as a benchmark protocol running in parallel with every screen. In screen 1, one hit compound was identified (LDN-193189) and was found to be most effective when added for the first 4 days followed by 4 days basal medium. For screen 2, two hit compounds were identified (Cyclopamine and IWP-2) when cells were first exposed to the hit compound from screen 1 for 4 days and hit compounds from screen 2 were added for the last 10 days of differentiation. The graph shows the % effect of the fraction of NKX6.1/PDX1 double positive cells compared to the Benchmark protocol (Bars for hiPSC in black and hESC in white).

LIST OF ABBREVIATIONS

Figure 1:
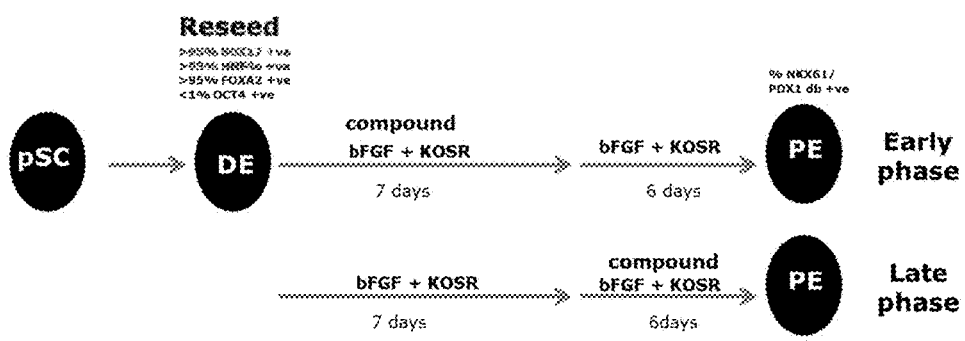
FIG. 1 shows the PE screening approach—also referred to as the library screening approach—using small molecule libraries. Pluripotent stem (PS) cells were differentiated into definitive endoderm (DE) according to the DE protocol (see general methods) and seeded in 96 well plates for screening. The pancreatic endoderm (PE) screen was divided into an early and a late phase. In the early phase compounds were added on top of a published bFGF based protocol (Ameri et al., 2010, cf. also WO/2010/136583) for the first seven days of PE differentiation and then continued for another six days without the compounds. In the late phase compounds were only added on top of the bFGF based protocol for the last six days.

+ve: positive
bFGF: basic Fibroblast Growth Factor (FGF) (also known as FGF2)
Cyc: Cyclopamine
db: double positive
DE: Definitive Endoderm
hBS: human Blastocyst derived Stem
hBSC; human Blastocyst-derived Stem Cells
hES: human Embryonic Stem
hESC: human Embryonic Stem Cells
hiPSC: human induced Pluripotent Stem Cells
hPSC: human Pluripotent Stem Cells
KOSR: Knock-out Serum Replacement
NKX6.1: NK6 homeobox 1
PDX1: Pancreatic and duodenal homeobox 1
PEST: Penicillin Streptomycin
PS: Pluripotent Stem
Rockout: Rho Kinase Inhibitor III
RT: Room Temperature Description The present invention related to methods of generating pancreatic endoderm from stem cells, such as human definitive endoderm cells and induced pluripotent stem cells.

The present invention takes an alternative approach to improve the efficiency of differentiating human PS cells toward mature beta cells, by providing a method to improve the percentage of NKX6.1/PDX1 double positive cells, which are markers for a PE cell population, one of the cell stages necessary to reach endocrine cell populations.

Furthermore, the present invention provides a more homogenous and synchronised pancreatic cell population, which is important for the further development of these cells towards the endocrine lineage.

The present invention may also solve further problems that will be apparent from the disclosure of the exemplary embodiments.

In one embodiment, the pancreatic endocrine cells obtainable by the method according to the invention are insulin producing cells, optionally together with cells differentiated towards glucagon, somatostatin, pancreatic polypeptide, and/or ghrelin producing cells. As used herein, "insulin producing cells" refers to cells that produce and store or secrete detectable amounts of insulin. "Insulin producing cells" can be individual cells or collections of cells.

In another embodiment, the cell population comprising pancreatic cells is obtained from a somatic cell population. In some aspects the somatic cell population has been induced to de-differentiate into an embryonic-like stem (ES, e.g., a pluripotent) cell. Such de-differentiated cells are also termed induced pluripotent stem cells (iPSC).

In another embodiment, the cell population comprising pancreatic cells is obtained from embryonic stem (ES, e.g., pluripotent) cells. In some aspects the cell population comprising pancreatic cells is pluripotent cells such as ES like-cells.

In another embodiment, the cell population comprising pancreatic cells is embryonic differentiated stem (ES or pluripotent) cells. Differentiation takes place in embryoid bodies and/or in monolayer cell cultures or a combination thereof.

In another embodiment, the cell population is a population of stem cells. In some aspects the cell population is a population of stem cells differentiated to the pancreatic endocrine lineage.

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multi-potent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multi-potent stem cells; and (5) unipotent, meaning able to give rise to a single cell lineage (e.g., spermatogenic stem cells).

A protocol for obtaining pancreatic cells from stem cells is exemplified by, but not limited to, the protocols described in D'Amour, K. A. et al. (2006); Jiang, J. et al. (2007); Kroon, E. et al. (2008).

A protocol for obtaining pancreatic cells from somatic cells or somatic cells induced to de-differentiate into pluripotent cells such as ES like-cells is exemplified by, but not limited to, the protocols described in Aoi, T. et al. (2008); D'Amour, K. A. et al. (2006); Jiang, J. et al. (2007); Kroon, E. et al. (2008); Takahashi, K. et al. (2007); Takahashi, K., and Yamanaka, S. (2006) and Wernig, M. et al. (2007).

As used herein "differentiate" or "differentiation" refers to a process where cells progress from an undifferentiated state to a differentiated state, from an immature state to a less immature state or from an immature state to a mature state. For example, early undifferentiated embryonic pancreatic cells are able to proliferate and express characteristics markers, like PDX1, NKX6.1, and PTF1a. Mature or differentiated pancreatic cells do not proliferate and do secrete high levels of pancreatic endocrine hormones or digestive enzymes. E.g., fully differentiated beta cells secrete insulin at high levels in response to glucose. Changes in cell interaction and maturation occur as cells lose markers of undifferentiated cells or gain markers of differentiated cells. Loss or gain of a single marker can indicate that a cell has "matured or fully differentiated." The term "differentiation factor" refers to a compound added to pancreatic cells to enhance their differentiation to mature endocrine cells also containing insulin producing beta cells. Exemplary differentiation factors include hepatocyte growth factor, keratinocyte growth factor, exendin-4, basic fibroblast growth factor, insulin-like growth factor-1, nerve growth factor, epidermal growth factor platelet-derived growth factor, and glucagon-like peptide 1. In some aspects differentiation of the cells comprises culturing the cells in a medium comprising one or more differentiation factors.

As used herein, "human pluripotent stem cells" (hPSC) refers to cells that may be derived from any source and that are capable, under appropriate conditions, of producing human progeny of different cell types that are derivatives of all of the 3 germinal layers (endoderm, mesoderm, and ectoderm). hPSC may have the ability to form a teratoma in 8-12 week old SCID mice and/or the ability to form identifiable cells of all three germ layers in tissue culture. Included in the definition of human pluripotent stem cells are embryonic cells of various types including human blastocyst derived stem (hBS) cells in 30 literature often denoted as human embryonic stem (hES) cells, (see, e.g., Thomson et al. (1998), Heins et al. (2004), as well as induced pluripotent stem cells (see, e.g. Yu et al. (2007); Takahashi et al. (2007)). The various methods and other embodiments described herein may require or utilise hPSC from a variety of sources. For example, hPSC suitable for use may be obtained from developing embryos. Additionally or alternatively, suitable hPSC may be obtained from established cell lines and/or human induced pluripotent stem (hiPS) cells.

As used herein "hiPSC" refers to human induced pluripotent stem cells.

ES cell lines can also be derived from single blastomeres without the destruction of ex utero embryos and without affecting the clinical outcome (Chung et al. (2006) and Klimanskaya et al. (2006)).

As used herein, the term "blastocyst-derived stem cell" is denoted BS cell, and the human form is termed "hBS cells".

In literature the cells are often referred to as embryonic stem cells, and more specifically human embryonic stem cells (hESC). The pluripotent stem cells used in the present invention can thus be embryonic stem cells prepared from blastocysts, as described in e.g. WO 03/055992 and WO 2007/042225, or be commercially available hBS cells or cell lines. However, it is further envisaged that any human pluripotent stem cell can be used in the present invention, including differentiated adult cells which are reprogrammed to pluripotent cells by e.g. the treating adult cells with certain transcription factors, such as OCT4, SOX2, NANOG, and LIN28 as disclosed in Yu, et al. (2007); Takahashi et al. (2007) and Yu et al. (2009).

As used herein JNK inhibitor II includes isomers or tautomers of 1,9-pyrazoloanthrone with or without N-alkylation. Where 1,9-pyrazoloanthrone can be defined as "SMILES: c1ccc2c(c1)-c3c4c(cccc4[nH]n3)C2=O" or "1,6-dihydrodibenzo[cd,g]indazol-6-one".

DEF medium or DEF-CS medium/system is a defined balanced culture medium for the establishment and propagation of human pluripotent stem cells, DEF-CS medium/system.

Embodiments of the Invention
1. A method of producing pancreatic cells or pancreatic cell precursors where at least 5% of the cells co-express PDX1 and NKX6.1, comprising exposing embryonic stem cells to an effective amount of at least one compound of the group consisting of:
    a. BMP inhibitors
    b. kinase inhibitors
    c. retinoic acid receptor agonists
    to differentiate the human embryonic stem cells into the pancreatic cells or pancreatic cell precursors.
2. The method of embodiment 1, wherein said compounds are listed in tables 1 or 2.
3. The method of embodiments 1 or 2, wherein the kinase inhibitor is an isomer of 1,9-pyrazoloanthrone with or without N-alkylation.
4. The method of embodiments 1-3, wherein said kinase inhibitor is JNK inhibitor II.
5. The method of embodiments 1-2, wherein said retinoic acid receptor agonist is AM580.
6. The method of embodiments 1-5, wherein said JNK inhibitor II is in combination with AM580.
7. The method of embodiments 3-6, wherein bFGF is present.
8. The method of embodiments 7, wherein said bFGF is FGF2, FGF7 or FGF10.
9. The method of embodiment 8, wherein said bFGF is FGF7.
10. The method of embodiment 1, wherein said BMP inhibitor is LDN-193189.
11. The method of embodiment 10, wherein said LDN-193189 is followed by exposure to a Wnt inhibitor or a hedgehog inhibitor.
12. The method of embodiment 11, wherein said Wnt inhibitor is IWP2.
13. The method of embodiment 12, wherein said hedgehog inhibitor is cyclopamine.
14. The method of embodiments 1-13, wherein said pancreatic cells or pancreatic cell precursors are 10-20%, 10-30%, 10-40%, 5-20%, 5-30%, 5-40%, 5-50%, 5-60% or 5-70%, 5-80%, 40-80% or 5-90% PDX1/NKX6.1 double positive.
15. The method of any one of embodiments 14, wherein said pancreatic cells or pancreatic cell precursors are 5-50% PDX1/NKX6.1 double positive.
16. The method of any one of embodiments 1-9, wherein said pancreatic cells or pancreatic cell precursors are 40-80% PDX1/NKX6.1 double positive.
17. A pancreatic cell or pancreatic cell precursors obtainable by the methods of embodiments 1-16.
18. A pancreatic cell or pancreatic cell precursor produced by exposing a human pluripotent stem cell to at least one compound listed in Tables 1 or 2.
19. The pancreatic cell or pancreatic cell precursor of embodiment 18, in which said compound is LDN-193189.
20. The pancreatic cell or pancreatic cell precursor of embodiment 18, in which said compound is JNK inhibitor II.
21. The pancreatic cell or pancreatic cell precursor of embodiment 18, in which said compound is AM580.
22. The pancreatic cell or pancreatic cell precursor of embodiment 18, in which the pancreatic cell or pancreatic cell precursor is produced by exposing the stem cell to at least one compound in combination with at least one additional agent.
23. The pancreatic cell or pancreatic cell precursor of embodiment 22, in which said LDN-193189 is in combination with JNK inhibitor II and AM580.
24. The pancreatic cell or pancreatic cell precursor of embodiment 22, in which said LDN-193189 is followed by exposure to cyclopamine.
25. The pancreatic cell or pancreatic cell precursor of embodiment 22, in which said LDN-193189 is followed by exposure to IWP2.
26. The pancreatic cell or pancreatic cell precursor of embodiment 22, in which said compound is JNK inhibitor II in combination with a retinoic acid receptor agonist listed in Table 2.
27. The pancreatic cell or pancreatic cell precursor of embodiment 22, wherein JNK inhibitor II is in combination with AM580.
28. The pancreatic cell or pancreatic cell precursor of embodiment 22, wherein JNK inhibitor II is in combination with AM580 and bFGF.
29. The pancreatic cell or pancreatic cell precursor of embodiment 28, wherein bFGF is FGF2, FGF7 or FGF10.
30. The pancreatic cell or pancreatic cell precursor of embodiment 29, wherein bFGF is FGF7.
31. Use of a compound of Tables 1 or 2 to induce pancreatic cells or pancreatic cell precursors from stem cells.
32. Use of JNK inhibitor II to induce pancreatic cells or pancreatic cell precursors from stem cells.
33. Use of JNK inhibitor II in combination with a retinoic acid receptor agonist to induce pancreatic cells or pancreatic cell precursors from stem cells.
34. Use of JNK inhibitor II in combination with AM580 to induce pancreatic cells or pancreatic cell precursors from stem cells.
35. Use of LDN-193189 to induce pancreatic cells or pancreatic cell precursors from stem cells.
36. Use of LDN-193189 followed by Cyclopamine or IWP2 to induce pancreatic cells or pancreatic cell precursors from stem cells.
37. Use of LDN-193189 followed by Cyclopamine to induce pancreatic cells or pancreatic cell precursors from stem cells.
38. Use of LDN-193189 followed by IWP2 to induce pancreatic cells or pancreatic cell precursors from stem cells.

39. Use of LDN-193189 followed by combination with JNK inhibitor II, AM580 and bFGF to induce pancreatic cells or pancreatic cell precursors from stem cells.
40. Use of LDN-193189 followed by a combination of JNK inhibitor II, AM580, LDN-193189 and bFGF to induce pancreatic cells or pancreatic cell precursors from stem cells.
41. Use of LDN-193189 followed by a combination of JNK inhibitor II, AM580, LDN-193189, bFGF and Cyclopamine or IWP2 to induce pancreatic cells or pancreatic cell precursors from stem cells.
42. Use of LDN-193189 followed by a combination of JNK inhibitor II, AM580, LDN-193189, bFGF and Cyclopamine to induce pancreatic cells or pancreatic cell precursors from stem cells.
43. Use of LDN-193189 followed by a combination of JNK inhibitor II, AM580, LDN-193189, bFGF and IWP2 to induce pancreatic cells or pancreatic cell precursors from stem cells.
44. A method of producing pancreatic cells or pancreatic cell precursors expressing at least 5% PDX1/NKX6.1 double positive, comprising exposing definitive endoderm cells to an effective amount of at least one of the compounds from each of the following groups:
    a. BMP inhibitor, and
    b. Kinase inhibitors, and
    c. Retinoic acid receptor agonists
    to differentiate the definitive endoderm cells into the pancreatic cell or pancreatic cell precursors.
45. The method of embodiment 44 wherein the BMP inhibitor is LDN-193189.
46. The method of embodiment 44 wherein the retinoic acid receptor agonist is AM580.
47. The method of embodiment 44 wherein the retinoic acid receptor agonist is a retinoic acid derivative.
48. The method of embodiment 44 wherein the kinase inhibitor is an isomer of 1,9-pyrazoloanthrone with or without N-alkylation.
49. The method of embodiment 44 wherein the kinase inhibitor is JNK inhibitor II and is in combination with AM580.
50. The method of embodiment 44 wherein said kinase inhibitors and retinoic acid receptor agonists are in combination with bFGF.
51. The method of embodiment 44 wherein said kinase inhibitors and retinoic acid receptor agonists are in combination with FGF7 or FGF10.
52. The method of embodiments 44-46, comprising a first step of exposing definitive endoderm cells to an effective amount of LDN-193189, without bFGF, and a second step of exposure to JNK inhibitor II in combination with AM580, in the presence of bFGF.
53. The method of embodiments 44-46, comprising exposing definitive endoderm cells to an effective amount of LDN-193189, following exposure to at least one compound of the group consisting of:
    a wnt inhibitor, such as IWP2, and/or
    a hedgehog inhibitor, such as cyclopamine
54. The method of any one of embodiments 44-53, wherein said pancreatic cells or pancreatic cell precursors are at least 5%, at least 10%, 10-30%, 10-40%, 5-70%, 10-80% or 5-100% PDX1/NKX6.1 double positive.
55. A pancreatic cell or pancreatic cell precursor obtainable by in vitro use of the methods of embodiments 44-54.
56. A pancreatic cell or pancreatic cell precursor produced by in vitro exposing definitive endoderm cells to a kinase inhibitor targeting JNK1, 2 or 3, or Syc or Src or GSK-3 or P38 MAPK or P38 kinase or Rho kinase or MEK or Chk2 or VEGFR1, 2 or 3 or PDGFRb or KDR/Flk-1.
57. A pancreatic cell or pancreatic cell precursor produced by the method of embodiment 56 wherein the kinase inhibitor is JNK inhibitor II and wherein the definitive endoderm cells are also exposed to at least one of the following compounds:
    LDN-193189,
    a Wnt inhibitor,
    a hedgehog inhibitor,
    a retinoic acid receptor agonist.
58. The pancreatic cell or pancreatic cell precursor of embodiment 56 wherein the definitive endoderm cells are exposed to JNK inhibitor II in combination with a retinoic acid receptor agonist listed in Table 2.
59. Use of a kinase inhibitor compound of Table 1 or 2 to induce pancreatic cells or pancreatic cell precursors from a pancreatic endoderm precursor.
60. Use of JNK inhibitor II and LDN-193189 in combination to induce pancreatic cells or pancreatic cell precursors from a pancreatic endoderm precursor.
61. Use of JNK inhibitor II in combination with a retinoic acid receptor agonist to induce pancreatic cells or pancreatic cell precursors from a pancreatic endoderm precursor.

General Methods

In Vitro Culture of Pluripotent Stem Cells

Human embryonic stem (hES) cells line SA121 and human induced pluripotent stem cells (hiPSC) chIPS4 (Cellectis) were grown in DEF-CS culture media (Cellectis) in T75 culture flasks. Cells were single cell passaged with 5 µM Rock inhibitor Y-27632 (Sigma #Y0503) and seeded at a density of 40000 cells/cm2 for experiments. Cells were cultured at 37° C. and 5% $CO_2$ in a humidified incubator (ThermoScientific Model 371).

In Vitro Differentiation of Pluripotent Stem Cells into Definitive Endoderm

Confluent cultures of hES cells (line SA121) and hiPSC (chIPS4) were washed once in RPMI1640 (Gibco #61870) and treated with 3 µM CHIR99021 (Axon#1386) in RPMI1640. After 24 hours the cells were washed with RPMI1640 and treated with 100 ng/ml Activin A (Peprotech #120-14E) in RPMI1640. 24 hours later, 2% B27 (Invitrogen #17504-044) was added to the Activin A media for 2 days with daily media change. Cells were maintained at 37° C. and 5% $CO_2$ in a humidified incubator during the differentiation.

Seeding of hES and hiPS Cell Derived Definitive Endoderm.

Human ES cell derived DE and Human iPS cell derived DE cells were washed in PBS−/− and trypsinized for 5 min. using Tryple Select (Invitrogen, 12563-029). DE cells were carefully suspended in RPMI1640 and washed once before they were resuspended in DE seeding medium (Activin A 100 ng/ml, 2% B27, RPMI1640, 0.1% PEST (Gibco #15140)). The DE cells were seeded at 200 000/cm$^2$ in 96 well optical plates (BD Bioscience), and PE differentiation using screening compounds was initiated the following day.

Analysis

At day 8 or 14 of PE differentiation, media were aspirated followed by fixation of the cells at room temperature for 30 min with 4% paraformaldehyde (VWR, 97.131.000). Cells were washed with PBS and permeabilized with 0.5% Triton X-100 (Sigma, 9002-93-1) for 10 min, washed and blocked in 0.5% TNB-buffer (Perkin Elmer) for 30 min at room temperature. Primary antibodies mouse anti-NKX6.1 (Abcore#A55F12) and goat anti-PDX1 (Abcam#47383) were diluted 1:500 and 1:8000, respectively, in 0.1% Triton X-100 in PBS and added to each well for overnight incubation at 4° C. Cells were washed three times with PBS. DAPI (4',6-diamidino-2-phenylindole, Applichem, A4099.0010) and secondary antibodies, Alexa Fluor 488 donkey anti-goat and Alexa Fluor 594 donkey anti-mouse (both Invitrogen) were diluted 1:1000 in 0.1% Triton X-100 in PBS and added to each well for 45 min. Cells were washed five times and left in 200 µL PBS for imaging.

Imaging was performed using the InCell Analyzer 2000 (GE Healthcare). 4 fields per well with 10× objective were captured. The total cell number based in the DAPI counterstaining and the number of NKX6.1/PDX1 double positive cells was determined using InCell Developer Toolbox 1.8 (GE Healthcare). The fraction of NKX6.1/PDX1 double positive cells was normalized to the benchmark on each plate and the % effect was calculated. Values above 200% effect were categorized as hits.

EXAMPLES

Pancreatic endoderm is characterized by co-expression of two transcription factors, NKX6.1 and PDX1. Many of the published protocols for making PE are ineffective with low outcome of NKX6.1/PDX1 double positive cells. Enhancing the efficacy of the PE protocols is a desirable outcome. We therefore screened libraries of small molecules to identify novel compounds that would improve the existing PE protocols. This was done on the assumption that inhibitors, agonists or antagonists may regulate signaling pathways, or chromosomal accessibility, which would improve the fraction of NKX6.1/PDX1 double positive cells.

Example 1

Screening Small Molecules that Induce NKX6.1/PDX1 Co-Expression

Small Molecules

Four different libraries were included in the screen; a kinase inhibitor library (Calbiochem #539743), a bioactive lipid library (Enzo Life Sciences #BML-2800), a nuclear receptor ligand library (Enzo Life Sciences # BML-2802) and a phosphatase inhibitor library (Enzo Life Sciences #BML-2834). The compounds within the bioactive library were tested at 1 uM and 0.1 uM. Compounds from the other libraries were tested at 10 uM and 1 uM. In a second candidate based screening approach, small molecules that target the main signalling pathways involved in pancreas development were included.

NKX6.1/PDX1 Screen

The library compounds were screened on top of a bFGF based media formulation for making PE (Ameri et al. 2010) (RPMI1640, Gibco#61870; 12% KOSR, Gibco#10828; 0.1% PEST, Gibco#15140; 64 ng/mL bFGF, Peprotech #100-18B).

The library PE screening approach was divided into an early and a late phase (FIG. 1).

In the early phase, compounds were tested on top of the PE media for the first seven days of PE differentiation, and then the differentiation was continued for additional six days using PE media without compounds.

Figure 2:
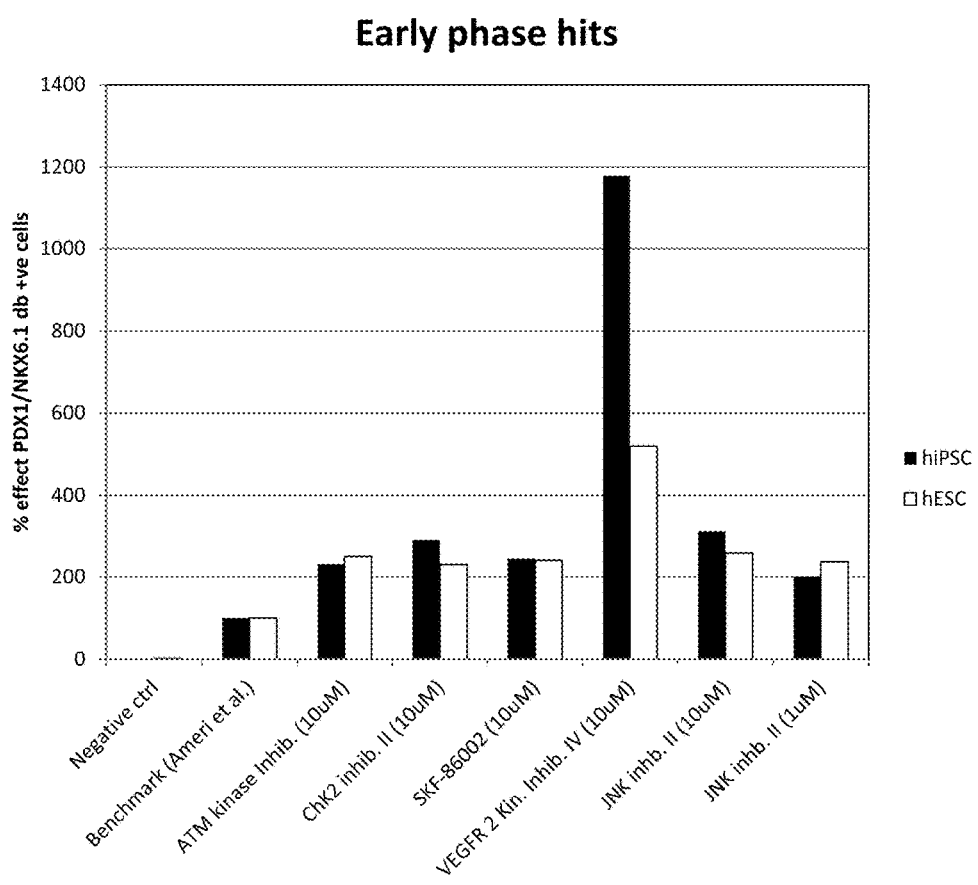
FIG. 2 shows early phase hits for the library screening approach. Definitive endoderm cells from human induced pluripotent stem cells (hiPSC) (black) or hESC (white) were seeded in 96 well optical plates and differentiated into pancreatic endoderm using a 14 day protocol based on bFGF. Compounds were added on top of the bFGF based protocol for the first seven out of 14 days and analysed for NKX6.1/PDX1 double positive cells using the InCell analyzer 2000 (GE Healthcare). The graph shows the % effect of the fraction of NKX6.1/PDX1 double positive cells compared to the Benchmark protocol.
Figure 3:
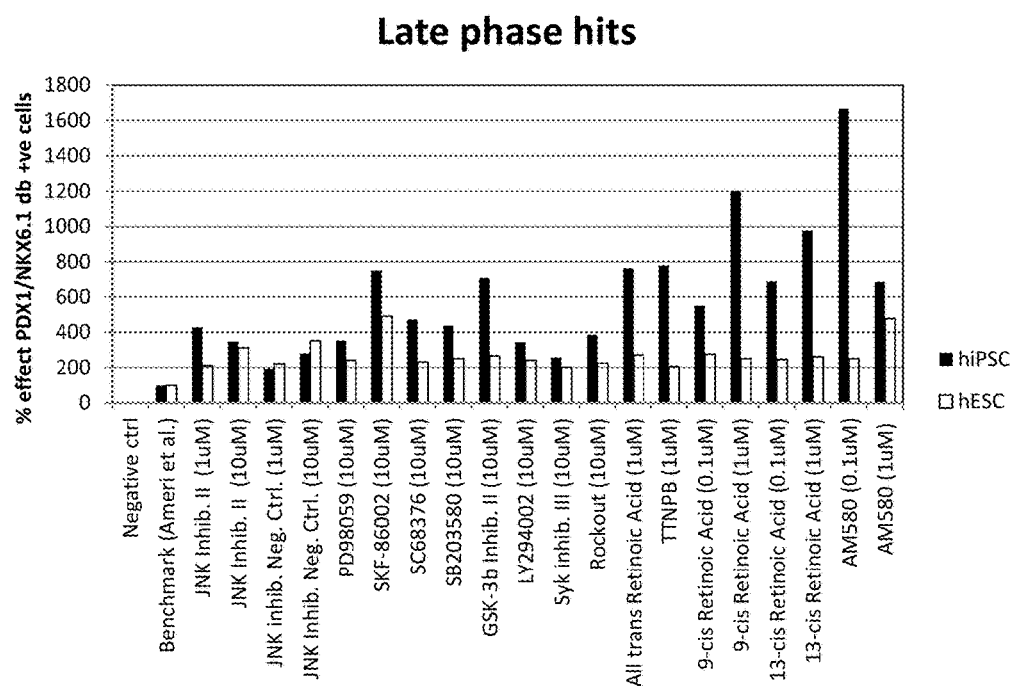
FIG. 3 shows late phase hits for the library screening approach. Definitive endoderm cells from hiPSC (black) or hESC (white) were seeded in 96 well optical plates and differentiated into pancreatic endoderm using a 14 day protocol based on bFGF. Compounds were added on top of the bFGF based protocol for the last six days and analysed for NKX6.1/PDX1 double positive cells using the InCell analyzer 2000 (GE Healthcare). The graph shows the % effect of the fraction of NKX6.1/PDX1 double positive cells compared to the Benchmark protocol.

In the late phase, DE cells were differentiated in the PE media for the first seven days. In the following six days compounds were tested on top of the PE media. 12 positive control wells (PE media) and 12 negative control wells (PE media without bFGF) were included in each 96 well plate. Media change was performed daily. Hits identified in the early phase screen are illustrated in FIG. 2 and listed in table 1. Hits identified in the late phase screen are illustrated in FIG. 3 and listed in table 2.

The compounds from the candidate approach were screened in basal medium (RPMI1640, Gibco#61870; 12% KOSR, Gibco#10828; 0.1% PEST, Gibco#15140) without the addition of bFGF. This candidate approach screen was divided into two parts (FIG. 4). In the first part, compounds were tested in time intervals with 2 day increments for the first eight days of PE differentiation (2 days exposure to compounds followed by 6 days basal medium or 4 days exposure to compounds followed by 4 days basal medium or 6 days exposure to compounds followed by 2 days basal medium or 8 days exposure to compounds).

One plate was fixed after these 8 days and analysed for PDX1 and NKX6.1 expression. A second plate was further differentiated for additional six days using the published PE protocol (Ameri et al. (2010)).

In the second part, DE cells were differentiated according to the hit compounds from the first part, the following 6-10 days compounds were tested in basal media.

The benchmark protocol (Ameri et al. (2010)) served as a control.

Media change was performed daily in both first and second part experiments.

Hits identified in the candidate screening approach are illustrated in FIG. 5 and also contained in Tables 1 and 2.

Example 2

Combining Small Molecule Hits that Induce NKX6.1/PDX1 Co-Expression

Figure 6:
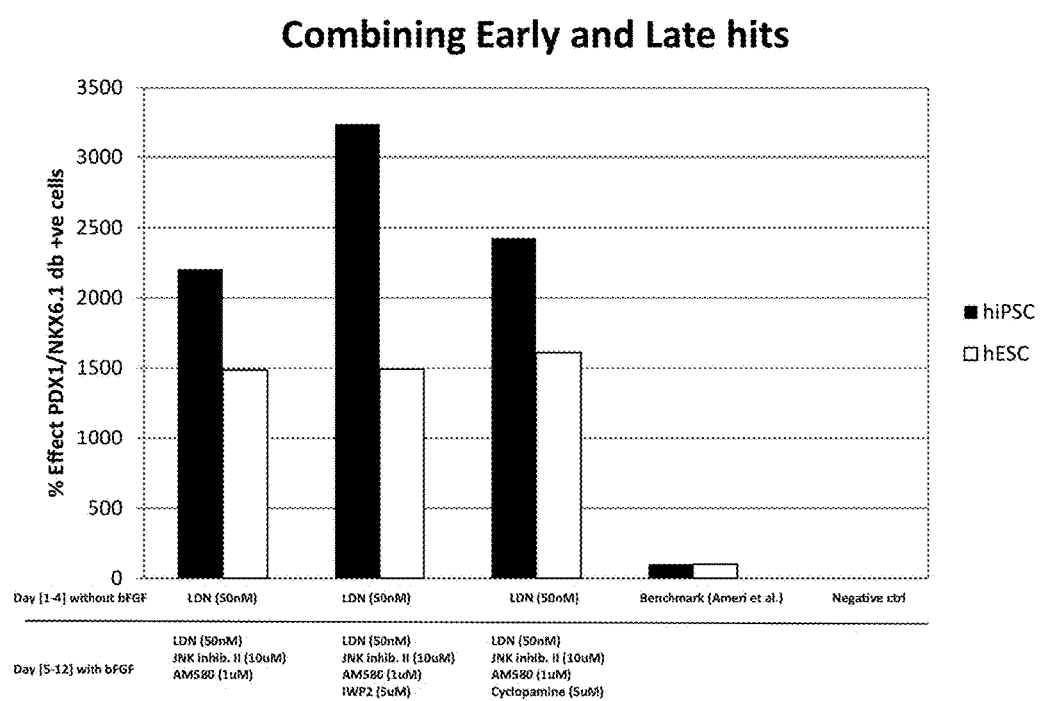
FIG. 6 shows the advantageous effect on the amount of PDX1/NKX6.1 double positive cells by the combination of hit compounds found in the two individual screens (small molecule libraries and candidate approach) compared to the benchmark protocol (Ameri et al. (2010)). Bars for hiPSC in black and hESC in white.

Combining Hits from the Candidate Screening Approach with Hits from the Library Approach DE cells were exposed to 4 days 50 nM LDN-193189, followed by 8 days AM580 (AH Diagnostics, BML GF104 0025), JNK Inhibitor II (Calbiochem, 420119), 50 nM LDN-193189 and 64 ng/ml FGF2, or AM580, JNK Inhibitor II, 50 nM LDN-193189, 64 ng/ml FGF2 and IWP2, or AM580, JNK Inhibitor II, 50 nM LDN-193189, 64 ng/ml FGF2 and Cyclopamine (FIG. 6). Media change was performed daily.

Example 3

Confirmation of Small Molecules that Induce NKX6.1/PDX1 Co-Expression in Human Induced Pluripotent Stem Cells Hit compounds (Tables 1 and 2) were screened on top of a bFGF based media formulation for making PE (Ameri et al. 2010) (RPMI1640, Gibco#61870; 12% KOSR, Gibco#10828; 0.1% PEST, Gibco#15140; 64 ng/mL bFGF, Peprotech #100-18B).

The screen was divided into an early and a late phase (FIG. 1). In the early phase, compounds were tested on top of the PE media for the first seven days of PE differentiation, and then continued for additional six days using PE media without compounds. In the late phase, DE cells were differentiated in the PE media for the first seven days. In the following six days compounds were tested on top of the PE media. Twelve positive control wells (PE media) and 12 negative control wells (PE media without bFGF) were included in each 96 well plate. Media change was performed daily.

Values above 200% effect were categorized as a hit (FIG. 2 and FIG. 3).

Table 1 shows early hit compounds.

Compounds that enhance the fraction of NKX6.1/PDX1 double positive cells more than 200% compared the PE media. Library, location of compound within the library, target, chemical structure, hit concentration and percentage of PDX1/NKX6.1 double positive cells are listed.

TABLE 1

Early phase hits.

| Library | Plate location | Target | Inhibitor | Structure | Concentration |
|---|---|---|---|---|---|
| Kinase inhibitor | B3 | ATM kinase | ATM Kinase Inhibitor | | 10 uM |
| Kinase inhibitor | D18 | Chk2 | Chk2 Inhibitor II | | 10 uM |
| Kinase inhibitor | N15 | P38 MAPK | SKF-86002 | | 10 uM |
| Kinase inhibitor | P20 | KDR/Flk-1, VEGFR-2, PDGFRb, VEGFR-1, VEGFR-3 | VEGF Receptor 2 Kinase Inhibitor IV | | 10 uM |
| Kinase inhibitor | H22 | JNK1, JNK2, JNK3 | JNK Inhibitor II | | 10 uM |
| Kinase inhibitor | H22 | JNK1, JNK2, JNK3 | JNK Inhibitor II | | 1 uM |

TABLE 1-continued

Early phase hits.

| Library | Plate location | Target | Inhibitor | Structure | Concentration |
|---|---|---|---|---|---|
| Candidate screen BMP inhibitor | Candidate approach | ALK2, ALK3, ALK6 | LDN-193189 | 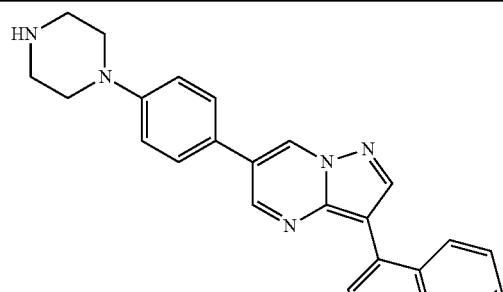 | 50 nM/ 100 nM |

Table 2 shows late hit compounds. Compounds that enhance the fraction of NKX6.1/PDX1 double positive cells more than 200% compared the PE media. Library, location of compound within the library, target, chemical structure, hit concentration and percentage of PDX1/NKX6.1 double positive cells are listed.

TABLE 2

Late phase hits.

| Library | Plate location | Target | Inhibitor | Structure | Concentration |
|---|---|---|---|---|---|
| Kinase inhibitor | H22 | JNK1, JNK2, JNK3 | JNK Inhibitor II | 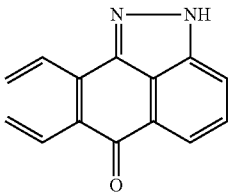 [SMILES: C=CC1=C(C=C)c2n[nH]c3cccc(c23)C1=O] | 10 uM |
| Kinase inhibitor | J4 | | JNK Inhibitor, Negative Control | 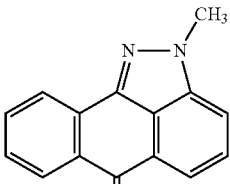 | 10 uM |
| Kinase inhibitor | P5 | syc, src | Syk Inhibitor III | 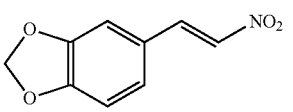 [SMILES: O=[N+]([O-])/C=C/c1ccc2c(c1)OCO2] | 10 uM |
| Kinase inhibitor | F20 | GSK-3 | GSK-3b Inhibitor II | 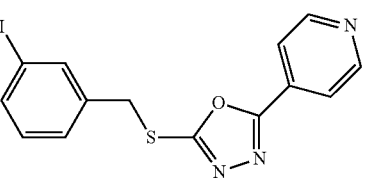 [SMILES: Ic1cccc(CSc2nnc(-c3ccncc3)o2)c1] | 10 uM |

TABLE 2-continued
Late phase hits.
| Library | Plate location | Target | Inhibitor | Structure | Concentration |
|---|---|---|---|---|---|
| Kinase inhibitor | N15 | P38 MAPK | SKF-86002 | 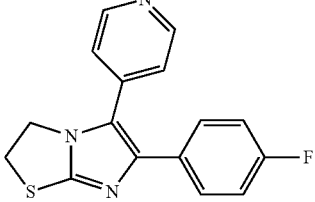 | 10 uM |
| Kinase inhibitor | J14 | PI3-kinase | LY 294002 | 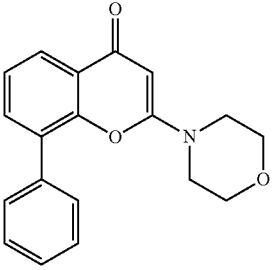 [SMILES: O=c1cc(N2CCOCC2)oc2c(-c3ccccc3)cccc12] | 10 uM |
| Kinase inhibitor | N14 | P38 MAPK | SC-68376 | 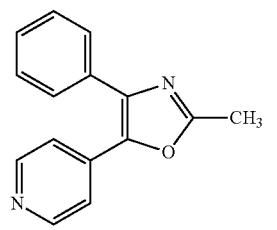 [SMILES: Cc1nc(-c2ccccc2)c(-c2ccncc2)o1] | 10 uM |
| Kinase inhibitor | N6 | Rho kinase | Rho Kinase Inhibitor III, Rockout | 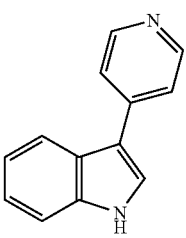 [SMILES: c1ccc2c(-c3ccncc3)c[nH]c2c1] | 10 uM |
| Kinase inhibitor | L5 | MEK | PD 98059 | 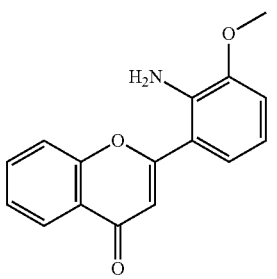 [SMILES: COc1cccc(-c2cc(=O)c3ccccc3o2)c1N] | 10 uM |
| Kinase inhibitor | N11 | P38 MAPK | SB 203580 | 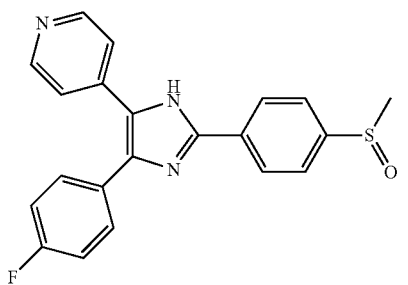 [SMILES: CS(=O)c1ccc(-c2nc(-c3ccc(F)cc3)c(-c3ccncc3)[nH]2)cc1] | 10 uM |

TABLE 2-continued

Late phase hits.

| Library | Plate location | Target | Inhibitor | Structure | Concentration |
|---|---|---|---|---|---|
| Bioactive lipids | 2-E09 | RAR | AM-580 | | 1 uM |
| Bioactive lipids | 2-E05 | RAR | RETINOIC ACID, ALL TRANS | | 1 uM |
| Bioactive lipids | 2-E07 | RAR/RXR | 13-CIS RETINOIC ACID | | 1 uM |
| Bioactive lipids | 2-E06 | RAR/RXR | 9-CIS RETINOIC ACID | | 1 uM |
| Bioactive lipids | 2-E10 | RAR | TTNPB | | 1 uM |
| Kinase inhibitor | H22 | JNK1, JNK2, JNK3 | JNK Inhibitor II | | 1 uM |
| Kinase inhibitor | J4 | | JNK Inhibitor, Negative Control | | 1 uM |

TABLE 2-continued

Late phase hits.

| Library | Plate location | Target | Inhibitor | Structure | Concentration |
|---|---|---|---|---|---|
| Bioactive lipids | 2-E09 | RAR | AM-580 | | 0.1 uM |
| Bioactive lipids | 2-E07 | RAR/RXR | 13-CIS RETINOIC ACID | | 0.1 uM |
| Bioactive lipids | 2-E06 | RAR/RXR | 9-CIS RETINOIC ACID | | 0.1 uM |
| Candidate screen Hedgehog pathway inhibitor | | Smoothened (SMO) | Cyclopamine | 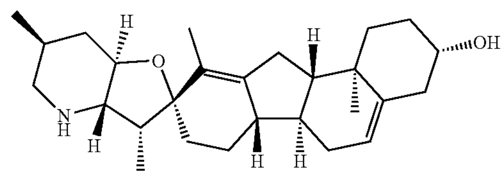 | 1 μM/5 μM |
| Candidate screen Wnt pathway inhibitor | | O-acyltransferase Porcupine | IWP2 | 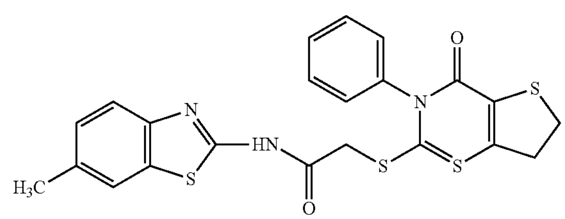 | 1 μM/5 μM |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

REFERENCES

Ameri et al. (2010) Stem Cells, 28:45-56

Cai J. et al. (2010). J Mol Cell Biol., February; 2(1):50-60

Chung Y. et al. (2006). Nature, January 12; 439(7073):216-9

D'Amour K. A. et al. (2006). Nat Biotechnol, 24: 1392-401

Heins N. et al. (2004). Stem Cells, 22(3):367-76

Jiang J. et al. (2007). Stem Cells, 25:1940-53

Kroon E. et al. (2008). Nat Biotechnol, 26:443-452

Klimanskaya I. et al. (2006). Nature, November 23; 444 (7118):481-5

Kunisada Y. et al. (2012). Stem Cell Res, 8(2):274-84

Schulz TC. et al. (2012). PLoS One, 7(5):e37004

Takahashi K. et al. (2007). Cell, 131:861-72

Takahashi K. and Yamanaka S. (2006). Cell, 126(4):663-76

Thomson JA. et al. (1998). Science, November 6; 282 (5391):1145-7

Wernig, M. et al. (2007). Nature, 448:318-24

Zhang D. et al. (2009). Cell Research, 19:429-438

The invention claimed is:

1. A method of producing pancreatic cells or pancreatic cell precursors, comprising a first exposure of definitive endoderm cells to an effective amount of at least one BMP inhibitor in the absence of bFGF, followed by a second exposure to JNK inhibitor II, bFGF, and at least one retinoic acid receptor agonist, wherein at least 5% of the resulting pancreatic cells or pancreatic cell precursors are PDX1NKX6.1 double positive.

2. The method of claim 1, wherein the at least one BMP inhibitor is

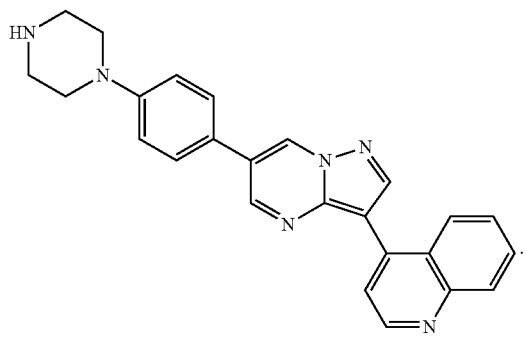 [SMILES: c1ccc2c(-c3cnn4cc(-c5ccc(N6CCNCC6)cc5)cnc34)ccnc2c1]

3. The method of claim 1, wherein the at least one retinoic acid receptor agonist is

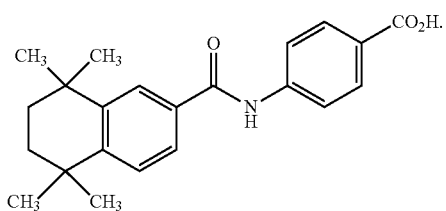 [SMILES: CC1(C)CCC(C)(C)c2cc(C(=O)Nc3ccc(C(=O)O)cc3)ccc21]

4. The method of claim 1, wherein the at least one retinoic acid receptor agonist is a retinoic acid derivative.

5. The method of claim 1, wherein the at least one BMP inhibitor is

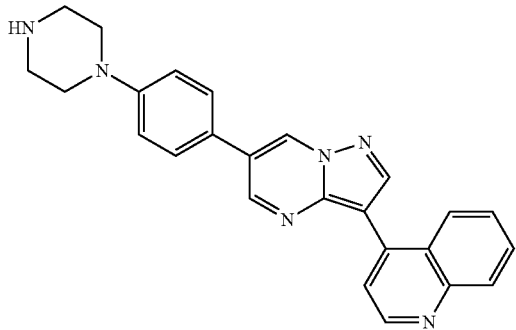 [SMILES: c1ccc2c(-c3cnn4cc(-c5ccc(N6CCNCC6)cc5)cnc34)ccnc2c1]

and the at least one retinoic acid receptor agonist is

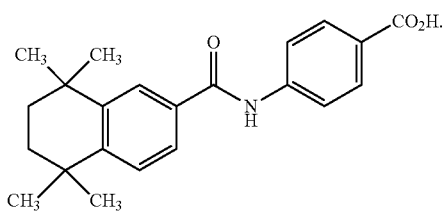 [SMILES: CC1(C)CCC(C)(C)c2cc(C(=O)Nc3ccc(C(=O)O)cc3)ccc21]

6. The method of claim 1, further comprising exposing the definitive endoderm cells to FGF7 or FGF10.

7. The method of claim 2, further comprising exposing the definitive endoderm cells to at least one compound selected from the group consisting of a wnt inhibitor and a hedgehog inhibitor prior to exposing the definitive endoderm cells to the

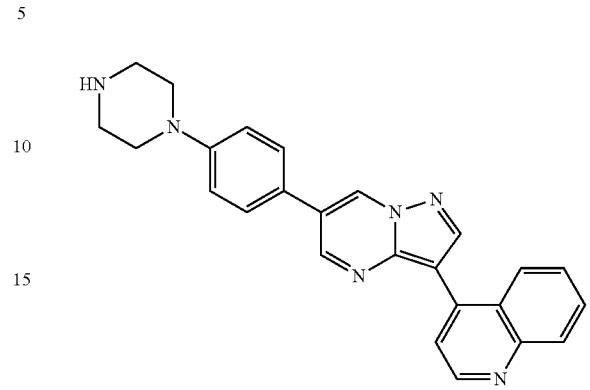

8. The method of claim 1, wherein said pancreatic cells or pancreatic cell precursors are at least 10% PDX1/NKX6.1 double positive.

9. A method of producing pancreatic cells or pancreatic cell precursors, comprising exposing definitive endoderm cells to an effective amount of at least one BMP inhibitor, JNK inhibitor II, bFGF, and at least one retinoic acid receptor agonist, wherein at least 5% of the resulting pancreatic cells or pancreatic cell precursors are PDX1NKX6.1 double positive.

10. The method of claim 9, wherein the at least one BMP inhibitor is

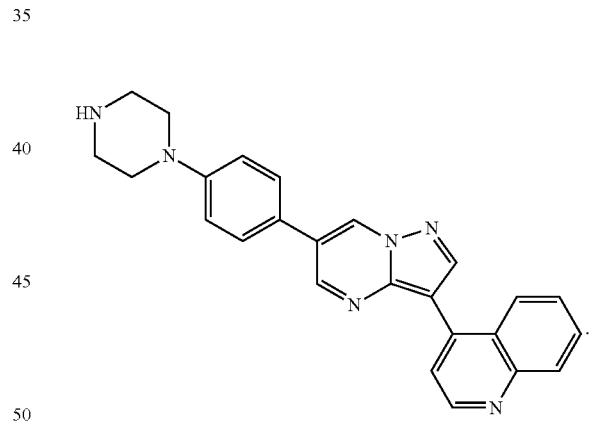

11. The method of claim 9, wherein the at least one retinoic acid receptor agonist is

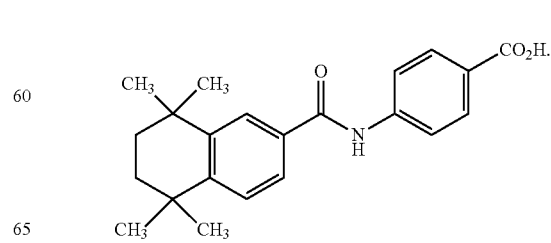

12. The method of claim 9, wherein the at least one BMP inhibitor is
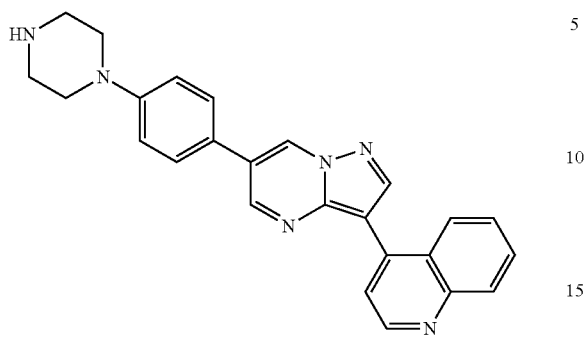
and the at least one retinoic acid receptor agonist is
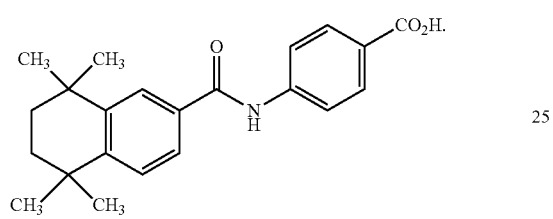
* * * * *